United States Patent [19]

Hendriksen

[11] 4,174,960

[45] Nov. 20, 1979

[54] PESTICIDAL FORMULATION

[75] Inventor: Barry A. Hendriksen, Bracknell, England

[73] Assignee: Lilly Industries Limited, Henrietta Place, United Kingdom

[21] Appl. No.: 874,599

[22] Filed: Feb. 2, 1978

[51] Int. Cl.$^2$ .............................................. A01N 17/00
[52] U.S. Cl. ................................. 71/121; 71/DIG. 1; 71/128
[58] Field of Search ................... 71/121, DIG. 1, 128

[56] References Cited

U.S. PATENT DOCUMENTS

| 1,914,969 | 6/1933 | Chipman | 71/128 |
| 3,449,111 | 6/1969 | Wright et al. | 71/121 |
| 3,672,864 | 6/1972 | Maravetz | 71/103 |

OTHER PUBLICATIONS

Shibe, Jr. et al., Chem. Abst., vol. 65, (1966).

Saito et al., Chem. Abst. vol. 67 (1967).

*Primary Examiner*—Catherine L. Mills
*Attorney, Agent, or Firm*—Leroy Whitaker; Arthur R. Whale

[57] ABSTRACT

There are described novel pesticidal formulations in concentrate form which are aqueous emulsions containing 10% to 75% by weight of an herbicidal 2,6-dinitroaniline derivative, such as trifluralin, up to 60% by weight of water-immiscible solvent, 0.5% to 10% by weight of an emulsifying agent and 15% to 70% by weight of an aqueous solution of an inorganic salt, such as sodium chloride. The concentration of the inorganic salt in the aqueous solution is at least 5% by weight. The aqueous solution may additionally contain urea. The novel formulations are readily dispersible in large volumes of water in preparation for spraying and present a reduced fire risk compared with conventional concentrated formulations of 2,6-dinitroaniline herbicides.

18 Claims, No Drawings

PESTICIDAL FORMULATION

This invention relates to pesticidal formulations, and more particularly to herbicidal formulations in the form of aqueous emulsions containing high concentrations of herbicidal 2,6-dinitroaniline derivatives, such as trifluralin, and to methods of making such formulations.

Herbicidal 2,6-dinitroaniline derivatives characteristically possess a melting point which is less than 200° C. and a solubility in water at 25° C. which is less than 100 parts per million by weight. Such herbicidal derivatives have hitherto been formulated in a concentrated solution in a substantially water-immiscible organic solvent such as xylene, together with an emulsifying agent. These concentrated formulations are dispersed in large volumes of water prior to spraying on crop land.

The preparation of 2,6-dinitroaniline derivatives, such as trifluralin, and their activity as pre-emergent herbicides is described in, for example, U.K. Pat. No. 917,253.

Although the known concentrated formulations of herbicidal 2,6-dinitroaniline derivatives have proved to be highly effective in enabling large quantities of the pesticides to be stored in a relatively compact form whilst being readily dispersible in large volumes of water in preparation for spraying, they do suffer from the disadvantage that bulk storage of such formulations carries the unavoidable fire risk associated with storage of organic solvents, and the commercial penalty of the high cost of organic solvents. Hitherto it has not been possible to provide an aqueous pesticidal formulation containing a high concentration of a herbicidal 2,6-dinitroaniline derivative and having satisfactory storage stability.

According to the present invention there is provided a herbicidal formulation in concentrate form being an aqueous emulsion comprising 10% to 75% by weight of a herbicide being at least one herbicidal 2,6-dinitroaniline derivative having a solubility in water at 25° C. less than 100 parts per million by weight and a melting point in the range from −10° C. to 150° C., 0% to 60% by weight of a substantially water-immiscible solvent, the herbicide and the solvent forming a homogeneous disperse phase, 0.5% to 10% by weight of an emulsifying agent, and 15% to 70% by weight of an aqueous solution of an inorganic salt, the concentration of the inorganic salt in the aqueous solution being at least 5% by weight.

The herbicide may be a single herbicidal 2,6-dinitroaniline derivative or a mixture or two or more such derivatives. If the herbicide is a mixture of 2,6-dinitroaniline derivatives, it is the mixture which must fulfil the melting point and water-solubility requirements.

Similarly the inorganic salt may be a single salt, such as sodium chloride, a double salt, such as sodium alum, or a mixture of salts. The salt should be such that the aqueous solution is substantially neutral, i.e. it has a pH not greater than 9. Examples of salts which have been found to be useful include sodium chloride, potassium chloride, ammonium chloride, calcium chloride, magnesium chloride, ammonium nitrate, sodium acetate, ammonium carbonate, copper sulphate, magnesium sulphate, sodium sulphate, aluminum sulphate, sodium ferric sulphate and potassium dihydrogen phosphate. Salts giving rise to strongly alkaline aqueous solutions, i.e. solutions having a pH greater than 9, such as sodium carbonate, potassium carbonate and potassium monohydrogen phosphate should be avoided.

The emulsifying agent may consist of a single emulsifying agent or it may be a blend of emulsifying agents, and it may be a non-ionic, anionic or cationic surfactant, a blend of two or more non-ionic surfactants, a blend of non-ionic and anionic surfactants or a blend of non-ionic and cationic surfactants. Non-ionic surfactants are preferred. The hydrophile-lipophile balance (HLB) of the emulsifying agent should be at least 12.

The substantially water-immiscible solvent may be a single organic solvent or it may be a blend of two or more such materials. It is essential for the solvent to be such as will dissolve the herbicide in the formulation and to be substantially immiscible with the aqueous phase of the emulsion. Desirably the solvent should not be soluble in the aqueous phase to an extent greater than 0.2% w/w, and preferably the solubility of the solvent in the aqueous phase is 0.2% w/w or less. The solvent may have a melting point at or above ambient temperatues. However, if this is the case, a mixture of the herbicide and the solvent in relative proportions equal to their relative proportions in the herbicidal formulation should desirably be liquid at ambient temperature. Examples of suitable solvents include aromatic hydrocarbons, such as xylenes, trimethylbenzenes and polynuclear aromatic hydrocarbons, such as naphthalene, alkylnaphthalenes and anthracene, halogenated aromatic hydrocarbons, such as o-chlorotoluene, aliphatic hydrocarbons, such as decane, and other organic solvents such as camphor, and miscible blends of two or more of such solvents. In the event that the herbicide is a liquid such as isopropalin, in some circumstances a herbicidal formulation according to the invention may not include any water-immiscible solvent other than the herbicide itself.

Preferably formulations in accordance with the invention contain from 15% to 70% by weight of the herbicide, from 0% to 45% by weight of the solvent, from 0.9% to 6% by weight of the emulsifying agent and from 20% to 40% by weight of the aqueous solution, the concentration of the inorganic salt in the aqueous solution being from 10% to 20% by weight.

Examples of suitable 2,6-dinitroaniline derivatives include trifluralin, (α,α,α-trifluoro-2,6-dinitro-N,N-dipropyl-p-toluidine) benfluralin, isopropalin, (2,6-dinitro-N,N-dipropylcumidine) ethalfluralin, dinitramine, dipropalin, oryzalin, 4-methylsulphonyl-2,6-dinitro-N,N-dipropylaniline, fluchloralin, penoxalin, profluralin and dibutalin. These derivatives fall within the scope of the formula I:

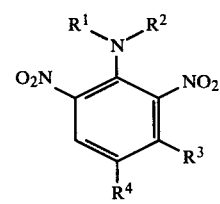

where $R^1$ is hydrogen, $C_{2-4}$ alkyl or chloroethyl, $R^2$ is $C_{2-5}$ alkyl, chloroethyl, 2-methallyl or cyclopropylmethyl, $R^3$ is hydrogen, methyl or amino and $R^4$ is trifluoromethyl, $C_{1-3}$ alkyl, $-SO_2NH_2$ or $-SO_2CH_3$.

Pesticidal formulations in accordance with the present invention preferably have one or more of the following features:

(a) the herbicide is a 2,6-dinitroaniline derivative of formula II:

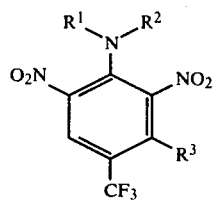

where $R^1$ is $C_{2-4}$ alkyl or chloroethyl, $R^2$ is $C_{2-4}$ alkyl, chloroethyl or 2-methallyl and $R^3$ is hydrogen or amino, (b) the herbicide is a 2,6-dinitroaniline derivative of formula II wherein $R^1$ is ethyl or propyl, $R^2$ is propyl, butyl or 2-methallyl and $R^3$ is hydrogen, (c) the herbicide is trifluralin, (d) the herbicide forms 15% to 65% by weight of the formulation, (e) the herbicide forms at least 40% by weight of the formulation, (f) the herbicide forms at least 45% by weight of the formulation, (g) the herbicide forms not more than 60% by weight of the formulation, (h) the solvent forms not more than 50% by weight of the formulation, (i) the solvent forms 10% to 45% by weight of the formulation, (j) the solvent forms at least 15% by weight of the formulation, (k) the solvent forms not more than 25% by weight of the formulation, (l) the solvent is an aromatic hydrocarbon solvent, (m) the solvent is xylene or a mixture of xylene and naphthalene, (n) the emulsifying agent forms at least 0.9% by weight of the formulation, (o) the emulsifying agent forms at least 2% by weight of the formulation, (p) the emulsifying agent forms at least 3% by weight of the formulation, (q) the emulsifying agent forms not more than 7% by weight of the formulation, (r) the emulsifying agent forms not more than 6% by weight of the formulation, (s) the emulsifying agent is a non-ionic surfactant or a blend of two or more non-ionic surfactants, (t) the emulsifying agent has a calculated hydrophile-lipophile balance of at least 12, (u) the emulsifying agent has a calculated hydrophile-lipophile balance in the range of from 14 to 18, (v) the emulsifying agent has a calculated hydrophile-lipophile balance in the range of from 15 to 17, (w) the emulsifying agent has a calculated hydrophile-lipophile balance of substantially 16, (x) the aqueous solution forms not more than 50% by weight of the formulation, (y) the aqueous solution forms not more than 40% by weight of the formulation, (z) the aqueous solution forms not more than 35% by weight of the formulation, (aa) the aqueous solution forms not more than 25% by weight of the formulation, (ab) the aqueous solution forms at least 10% by weight of the formulation, (ac) the aqueous solution forms at least 15% by weight of the formulation, (ad) the aqueous solution forms at least 20% by weight of the formulation, (ae) the aqueous solution additionally includes urea at a concentration up to 25% by weight of the aqueous solution, (af) the inorganic salt is selected from sodium chloride, potassium chloride and calcium chloride, (ag) the inorganic salt is sodium chloride.

When the herbicide is isopropalin it preferably forms 60% to 75% by weight of the formulation, no solvent is included, the emulsifying agent forms 2% to 6% by weight of the formulation and the aqueous solution forms 19% to 38% by weight of the formulation.

In accordance with a preferred aspect of the present invention there is provided a herbicidal formulation in concentrate form being an aqueous emulsion comprising:

45% to 60% by weight of trifluralin,

15% to 25% by weight of a substantially water-immiscible aromatic hydrocarbon solvent, the trifluralin and the solvent forming a homogeneous disperse phase, 3% to 6% by weight of a non-ionic surfactant or a blend of such surfactants, having a calculated hydrophile-lipophile balance in the range of from 15 to 17, and 22% to 32% by weight of an aqueous solution of sodium chloride, the sodium chloride concentration being in the range 10% to 18% by weight of the aqueous solution, the aqueous solution additionally including 0% to 5% of urea by weight of the solution.

The invention also provides a process for preparing a herbicidal formulation in concentrate form which process comprises agitating together a homogeneous organic phase containing 10% to 75% by weight of the formulation of a herbicide being at least one herbicidal 2,6-dinitroaniline having a solubility in water at 25° C. less than 100 parts per million by weight and a melting point in the range of from −10° C. to 150° C., and 0% to 60% by weight of the formulation of a substantially water-immiscible solvent, and an aqueous phase consisting of 15% to 70% by weight of the formulation of an aqueous solution of an inorganic salt, the concentration of the inorganic salt in the aqueous solution being at least 5% by weight, with 0.5% to 10% by weight of the formulation of an emulsifying agent, until a stable emulsion is formed therefrom.

In the method of the present invention, it is preferred for at least part of the emulsifying agent to be dissolved in the organic phase prior to agitation of the organic phase and the aqueous phase. The herbicide is preferably dissolved in the solvent, the resulting solution is filtered and the emulsifying agent is dissolved therein before addition thereto of the aqueous phase and agitation. The agitation is desirably continued until the mean droplet diameter of the organic phase is observed to be in the range 8 to 14 microns. Urea may be dissolved in the aqueous solution up to 5% by weight of the aqueous solution prior to agitation of the organic phase and the aqueous phase.

The invention further includes a method of inhibiting growth of weeds which method comprises dispersing in a large volume of water a herbicidal formulation according to the invention, and applying the dispersion formed thereby to a locus in which it is desired to inhibit the growth of weeds.

In the examples of the invention a number of emulsifying agents and solvents are referred to by their commercial names. The emulsifying agents are Remcopal NP 30, Remcopal PONF, Remcopal 25, Remcopal 0.11, Remcopal 273, Tensagex DP24, Stepan agent 555-66A, Stepan agent 555-66B, Ethomeen T.25, Renex 650, Brij 72 and Brij 78. The solvents are Aromasol H and Solvesso 100. The chemical natures of these commercial materials insofar as they are known to the Applicant are as follows:

Remocopal NP30—an ethoxylated nonyl phenol containing on average 30 ethoxy groups and having a hydrophile-lipophile balance (HLB) of 17.5, Remocopal PONF—an ethoxylated nonyl phenol containing on average 11 ethoxy groups and having an HLB of 13.7.

Remcopal 25—an ethoxylated oleo-cetyl alcohol containing on average 25 ethoxy groups and having an HLB of 16.2.

Remcopal 0.11—an ethoxylated octyl phenol containing on average 10.5 ethoxy groups and having an HLB of 13.8, Remcopal 273—an ethoxylated tridecylalcohol containing on average three ethoxy groups and having an HLB of 8.6, Stepan agents 555-66A and 555-66B—blends of calcium dodecylbenzene sulfonate and alkylphenoxy polyoxyethylene ethanols, Ethomeen T.25—ethylene oxide condensation product of primary fatty amines containing on average 15 ethoxy groups, Renex 650—an alkylaryl ether having an HLB of 17.1, Brij 72—a polyoxyethylene stearyl ether having an HLB of 4.9, Brij 78—a polyoxyethylene stearyl ether having an HLB of 15.3, Aromasol H—an aromatic hydrocarbon solvent consisting predominantly of isomeric trimethylbenzenes and having a specific gravity of 0.879 and distillation range from 168° C. to 200° C., Solvesso 100—an aromatic hydrocarbon solvent consisting predominantly of $C_9$ hydrocarbons but also containing some $C_8$ and $C_{10}$ hydrocarbon and having a specific gravity of 0.872 and distillation range from 156° C. to 180° C.

The invention will be better understood from the following illustrative Examples:

EXAMPLE 1

| | |
|---|---|
| Trifluralin, technical (96% pure) | 500 gms |
| Xylene | 230 gms |
| Emulsifying agent (blend of 24.4 gm "Remcopal NP30" and 15.6 gm "Remcopal PONF"). | 40 gms |
| Aqueous solution of sodium chloride (15% w/w) | 310 gms |
| TOTAL: | 1080 gms (1 litre) |

The trifluralin was dissolved in the xylene with gentle warming to 50° C. and the resulting solution was filtered through a fine grade (Whatman No. 42) filterpaper. The emulsifying agent was added to the solution of trifluralin in xylene, and dissolved with gentle warming to 50° C. The aqueous solution of sodium chloride was added to the xylene solution with agitation. The resulting emulsion was opaque and orange-yellow in colour.

EXAMPLE 2

| | |
|---|---|
| Trifluralin | 500 gms |
| Xylene | 180 gms |
| Naphthalene (technical grade) | 60 gms |
| Emulsifying agent as in Example 1 | 40 gms |
| Aqueous solution of sodium chloride (15% w/w) | 310 gms |
| TOTAL: | 1090 gms (1 litre) |

The trifluralin and naphthalene were dissolved in the xylene with gentle warming to 50° C., and the remaining steps in forming the emulsion were as in Example 1. The emulsion was opaque and orange-yellow in colour.

The formulations of Examples 1 and 2 were tested for stability by storing for one month at temperatures of −10° C., −2° C., room temperature, 40° C. and 50° C. There was no noticeable deterioration of the formulations under these conditions. Both formulations remained free flowing at −18° C., which was the lowest temperature at which they were tested.

Both emulsions flowed easily and were readily dispersed with slight agitation in large volumes of water.

EXAMPLE 3

A formulation was prepared in identical manner as in Example 1 except that the emulsifying agent used was 40 gms of Tensagex DP 24 supplied by Tensia S.A. This emulsifying agent is an anionic surfactant. The resulting formulation was a stable orange-yellow opaque emulsion.

EXAMPLE 4

A formulation was prepared as in Example 3 except that the emulsifying agent used was 40 gms of a blend of 75% by weight Stepan agent 555-66A and 25% by weight Stepan agent 555-66B supplied by Stepan Chemical Company. Both Stepan agents are blends of anionic and non-ionic surfactants. The resulting opaque emulsion was stable and was orange-yellow in colour.

EXAMPLE 5

A formulation was prepared as in Example 3, except that the emulsifying agent used was 40 gms of Ethomeen T.25 supplied by Armour Hess Chemicals Limited. This emulsifying agent is a cationic surfactant. The resulting emulsion was stable, was opaque in appearance, and was orange-yellow in colour.

EXAMPLE 6

A formulation was prepared as in Example 2, except that the aqueous solution was 310 gms of an aqueous solution of sodium chloride (17% w/w).

EXAMPLE 7

A formulation was prepared as in Example 1 except that the aqueous solution was 310 gms of an aqueous solution of sodium chloride (13% w/w) and urea (4% w/w).

EXAMPLE 8

A formulation was prepared as in Example 1, except that the aqueous solution was 310 gms of an aqueous solution of potassium dihydrogen phosphate (13% w/w).

EXAMPLE 9

A formulation was prepared as in Example 1 except that the aqueous solution was 310 gms of an aqueous solution of ammonium ferric sulphate (13% w/w).

EXAMPLES 10 to 15

Formulations were prepared as in Example 1 except that the following were used as the emulsifying agents:

| Ex. | Emulsifying Agent | |
|---|---|---|
| 10 | Remcopal 25 (36.7 gms) | + Remcopal 0.11 (3.3 gms) |
| 11 | Renex 650 (36.4 gms) | + Brij 72 (3.6 gms) |
| 12 | Renex 650 (15.6 gms) | + Brij 78 (24.4 gms) |
| 13 | Remcopal NP30 (18.3 gms) | + Remcopal PONF (11.7 gms) |
| 14 | Remcopal NP30 (12.2 gms) | + Remcopal PONF (7.8 gms) |
| 15 | Remcopal NP30 (6.1 gms) | + Remcopal PONF (3.9 gms) |

EXAMPLE 16

A formulation was prepared as in Example 1, except that in place of the xylene there was employed 235 gms of Solvesso 100.

EXAMPLE 17

A formulation was prepared as in Example 1, except that in place of the xylene there was employed 240 gms of Aromasol H.

EXAMPLE 18

| | |
|---|---|
| Trifluralin, technical (96% pure) | 625 gms |
| Xylene | 181 gms |
| Emulsifying agent (36.7 gms of Remcopal 25 and 3.3 gms of Remcopal 0.11) | 40 gms |
| Aqueous solution of sodium chloride (15% w/w) | 266 gms |
| TOTAL: | 1112 gms (1 litre) |

The above formulation was prepared by a similar method to that used in Example 1.

EXAMPLE 19

| | |
|---|---|
| Trifluralin, technical (96% pure) | 688 gms |
| Xylene | 119 gms |
| Emulsifying agent (24.4 gms of Remcopal NP30 and 15.6 gms of Remcopal PONF | 40 gms |
| Aqueous solution of sodium chloride (15% w/w) | 289 gms |
| TOTAL: | 1136 gms (1 litre) |

This formulation was prepared by a similar method to that used in Example 1.

The emulsions of Examples 6 to 19 were all stable emulsions opaque in appearance and orange-yellow in colour.

EXAMPLE 20

| | |
|---|---|
| Benfluralin, technical (95% pure) | 190 gms |
| Xylene | 317 gms |
| Naphthalene (technical grade) | 104 gms |
| Emulsifying agent (38.9 gms of Remcopal 25 and 1.1 gms of Remcopal 273) | 40 gms |
| Aqueous solution of ammonium chloride (13% w/w) | 362 gms |
| TOTAL: | 1013 gms (1 litre) |

The above formulation was prepared by a similar method to that used in Example 1. The resulting stable emulsion was opaque and was yellow in colour.

EXAMPLE 21

| | |
|---|---|
| Benfluralin, technical (95% pure) | 190 gms |
| Xylene | 277 gms |
| Cyclohexanone | 130 gms |
| Emulsifying agent (33.3 gms of Remcopal NP30 and 6.7 gms of Remcopal 273) | 40 gms |
| Aqueous solution of sodium chloride (15% w/w) | 362 gms |
| TOTAL: | 999 gms (1 litre) |

This formulation was prepared by a method similar to that used in Example 1. The resulting emulsion was identical in appearance to that of Example 20.

EXAMPLE 22

| | |
|---|---|
| Ethalfluralin, technical (95% pure) | 347 gms |
| Xylene | 361 gms |
| Emulsifying agent (33.3 gms of Remcopal NP30 and 6.7 gms of Remcopal 273) | 40 gms |
| Aqueous solution of sodium chloride (15% w/w) | 289 gms |
| TOTAL: | 1037 gms 1 litre) |

The above formulation was prepared by a similar method to that of Example 1. The resulting stable emulsion was opaque in appearance and yellow in colour.

EXAMPLE 23

A formulation was prepared as in Example 22, except that the aqueous solution was 282 gms of an aqueous solution of potassium chloride (13% w/w). The resulting emulsion was similar in appearance to that of Example 22.

EXAMPLE 24

A formulation was prepared as in Example 22 except that the aqueous solution was 289 gms of an aqueous solution of calcium chloride (13% w/w). The resulting emulsion was similar in appearance to those of Examples 22 and 23.

EXAMPLE 25

| | |
|---|---|
| Isopropalin, technical (90% pure) | 800 gms |
| Emulsifying agent (33.3 gms of Remcopal NP30 and 6.7 gms of Remcopal 273) | 40 gms |
| Aqueous solution of sodium chloride (15% w/w) | 338 gms |
| TOTAL: | 1178 gms (1 litre) |

The emulsifying agent was dissolved in the isopropalin with gentle warming. The aqueous solution of sodium chloride was added with agitation. The resulting stable emulsion was opaque and dirty orange-yellow in colour.

It should be noted that the emulsifying agent of each of Examples 1 to 25 has a calculated hydrophile-lipophile balance of substantially 16.

In the emulsions of Examples 1 to 25 above it has been found that the mean droplet diameter of the organic phase is in the range of from 8 to 14 microns. These emulsions have been found to disperse readily when added to 100 volumes of water and to remain substantially dispersed for several hours. Such dispersions are readily applied to crop land by conventional means such as spraying, and are therefore usable in a similar manner to the known concentrated formulations.

The emulsions of Examples 1, 2 and 4 to 25 exhibit particularly good stability under a variety of storage conditions. Coalescence of droplets and formation of upper or lower aqueous layers is very slow and samples may be stored for at least a year at 25° C. or 40° C. without appreciable coalescence. The emulsion of Example 7 has been found to have very good stability under high temperature storage conditions and has remained a stable emulsion after storage for several weeks at 60° C. At the lower ends of the temperature scale, these emulsions are generally stable at temperatures of $-2°$ C. to $-10°$ C. and exhibit good resistance to crystallisation. In general they do not freeze until the temperature drops to about $-25°$ C.

The formulations of Examples 1 to 25 present a reduced fire hazard compared with the known emulsifiable concentrate formulations of 2,6-dinitroaniline herbicides in organic solvents such as xylene.

We claim:

1. A herbicidal formulation in concentrate form being an aqueous emulsion comprising
    10% to 75% by weight of a herbicide being one or more herbicidal 2,6-dinitroaniline derivative having a solubility in water at 25° C. less than 100 parts per million by weight and a melting point in the range of from $-10°$ C. to 150° C.,
    0% to 60% by weight of a substantially water-immiscible solvent, the herbicide and the solvent forming a homogeneous disperse phase,
    0.5% to 10% by weight of an emulsifying agent, and
    15% to 70% by weight of an aqueous solution of an inorganic salt, the concentration of the inorganic salt in the aqueous solution and the pH of said aqueous solution being not greater than 9 being at least 5% by weight.

2. A formulation according to claim 1 which contains from 15% to 70% by weight of the herbicide, from 0% to 45% by weight of the solvent, from 0.9% to 6% by weight of the emulsifying agent and from 20% to 40% by weight of the aqueous solution, the concentration of inorganic salt in the aqueous solution being from 10% to 20% by weight.

3. A formulation according to claim 1 wherein no solvent is present, the herbicide is isopropalin which forms 60% to 75% by weight of the formulation, the emulsifying agent forms 2% to 6% by weight of the formulation and the aqueous solution forms 19% to 38% by weight of the formulation.

4. A formulation according to claim 1 which contains 15% to 65% by weight of the herbicide which is a 2,6-dinitroaniline derivative of formula

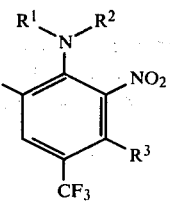

where $R^1$ is selected from the group consisting of $C_{2-4}$ alkyl and chloroethyl, $R^2$ is selected from the group consisting of $C_{2-4}$ alkyl, chloroethyl and 2-methallyl and $R^3$ is selected from the group consisting of hydrogen and amino, 10% to 45% by weight of the solvent, 0.9% to 6% by weight of the emulsifying agent, and 20% to 40% by weight of the aqueous solution.

5. A formulation according to claim 4 wherein $R^1$ is selected from the group consisting of ethyl and propyl, $R^2$ is selected from the group consisting of propyl, butyl and 2-methallyl and $R^3$ is hydrogen.

6. A formulation according to claim 1 wherein the herbicide is trifluralin which forms 40% to 65% by weight of the formulation, the solvent forms 10% to 25% by weight of the formulation, the emulsifying agent forms 0.9% to 6% by weight of the formulation and the aqueous solution forms 20% to 35% by weight of the formulation, the concentration of the inorganic salt being at least 10% by weight of the aqueous solution.

7. A formulation according to claim 6 wherein the trifluralin forms from 40% to 60% by weight of the formulation, the solvent forms from 15% to 25% by weight of the formulation, and the emulsifying agent forms from 2% to 6% by weight of the formulation.

8. A formulation according to claim 7 wherein the trifluralin forms from 40% to 50% of the formulation.

9. A formulation according to claim 1 wherein the water-immiscible solvent is xylene or a mixture of xylene and naphthalene.

10. A formulation according to claim 1 wherein the emulsifying agent is a non-ionic surfactant or a blend of two or more non-ionic surfactants.

11. A formulation according to claim 1 wherein the emulsifying agent has a calculated hydrophile-lipophile balance in the range of from 14 to 18.

12. A formulation according to claim 11 wherein the calculated hydrophile-lipophile balance is in the range of from 15 to 17.

13. A formulation according to claim 12 wherein the calculated hydrophile-lipophile balance is substantially 16.

14. A formulation according to claim 1 wherein the inorganic salt forms substantially 15% of the aqueous solution.

15. A formulation according to claim 1 wherein the inorganic salt is selected from sodium chloride, potassium chloride and calcium chloride.

16. A formulation according to claim 15 wherein the inorganic salt is sodium chloride.

17. A formulation according to claim 1 wherein the aqueous solution additionally includes urea at a concentration up to 25% by weight.

18. A herbicidal formulation in concentrate form being an aqueous emulsion comprising:
    45% to 60% by weight of trifluralin,
    15% to 25% by weight of substantially water-immiscible aromatic hydrocarbon solvent, the trifluralin and the solvent forming a homogeneous disperse phase, 3% to 6% by weight of a non-ionic surfactant or a blend of such surfactants, having a calculated hydrophile-lipophile balance in the range of from 15 to 17, and 22% to 32% by weight of an aqueous solution of sodium chloride, the sodium chloride concentration being in the range 10% to 18% by weight of the aqueous solution, the aqueous solution additionally including 0% to 5% of urea by weight of the solution.

* * * * *

UNITED STATES PATENT AND TRADEMARK OFFICE
CERTIFICATE OF CORRECTION

PATENT NO. : 4,174,960

DATED : November 20, 1979

INVENTOR(S) : Barry A. Hendriksen

It is certified that error appears in the above-identified patent and that said Letters Patent are hereby corrected as shown below:

Column 1, line 53, "or" second occurrence should read --of--.

Claim 1, lines 50-52, "salt in the aqueous solution and the pH of said aqueous solution being not greater than 9 being at least 5% by weight." should read --salt in the aqueous solution being at least 5% by weight and the pH of said aqueous solution being not greater than 9.--.

Signed and Sealed this

Eleventh Day of March 1980

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,174,960
DATED : November 20, 1979
INVENTOR(S) : Barry A. Hendriksen It is certified that error appears in the above-identified patent and that said Letters Patent are hereby corrected as shown below:

On the first page in the heading, please insert the following:

--[30]   Foreign Application Priority Data

February 9, 1977   United Kingdom ...... 5319/77 --

Signed and Sealed this

Twenty-seventh Day of May 1980

[SEAL]

Attest:

SIDNEY A. DIAMOND

Attesting Officer       Commissioner of Patents and Trademarks